United States Patent [19]

Coe et al.

[11] Patent Number: 5,491,234
[45] Date of Patent: Feb. 13, 1996

[54] PYRIMIDINE DERIVATIVES FOR ENHANCING ANTITUMOR ACTIVITY

[75] Inventors: Jotham W. Coe, Mystic; Anton F. J. Fliri, Norwich; Takushi Kaneko, Guilford; Eric R. Larson, Mystic, all of Conn.

[73] Assignee: Pfizer Inc., New York, N.Y.

[21] Appl. No.: 129,196

[22] PCT Filed: Mar. 30, 1992

[86] PCT No.: PCT/US92/02434

§ 371 Date: Oct. 14, 1993

§ 102(e) Date: Jan. 31, 1994

[87] PCT Pub. No.: WO92/18498

PCT Pub. Date: Oct. 29, 1992

[51] Int. Cl.⁶ .................. C07D 239/02; C07D 401/04; A61K 31/505
[52] U.S. Cl. .................... 544/325; 544/298; 544/324
[58] Field of Search .................... 544/324, 325, 544/298; 514/256, 275

[56] References Cited

U.S. PATENT DOCUMENTS

| | | | |
|---|---|---|---|
| 3,670,077 | 6/1972 | Freeman et al. | 544/323 |
| 3,974,162 | 8/1976 | Santilli et al. | 544/323 |
| 4,003,699 | 1/1977 | Rose et al. | 544/323 |
| 4,945,093 | 7/1990 | Maignan et al. | 544/122 |

FOREIGN PATENT DOCUMENTS

| | | |
|---|---|---|
| 0379806 | 8/1990 | European Pat. Off. . |
| 9112006 | 1/1991 | WIPO . |

OTHER PUBLICATIONS

M. Naito et al., Cancer Chemother. Pharmacol., (1992) 29:195–200.
D. Boesch et al., Cancer Research, 51, 4226–4233, Aug. 15, 1991.
P. R. Twentyman, Eur. J. Cancer, vol. 27, No. 12, pp. 1639–1642, 1991.
T. Kaneko, Current Opinion in Therapeutic Patents, Jul. 1991.
D. Hochhauser et al., Brit. Med. Bull., 47, 178–190, 1991.
W. T. Bellamy et al., Cancer Invest., 8, 547–562, 1990.
Gottesman et al., J. Biol. Chem., vol. 263, No. 25, pp. 12163–12166, 1988.
Fojo et al., Cancer Research, 45, 3002–3007, Jun. 1985.
Sonneveld et al., The Lancet, vol. 340, No. 8814, pp. 255–259 (1992).
T. Tsuruo, Xenobiotics and Cancer, L. Ernster et al., (Eds.), Japan Sci. Soc. Press Tokyo/Taylor and Francis Ltd., London, pp. 241–251, 1991.
W. S. Dalton et al., Cancer Invest., 8, 547–562 (1990).

*Primary Examiner*—Cecilia Tsang
*Attorney, Agent, or Firm*—Peter C. Richardson; Gregg C. Benson; John D. Conway

[57] ABSTRACT

2,4-diaminopyrimidine derivatives as potentiators of chemotherapeutic agents in the treatment of cancer.

14 Claims, No Drawings

PYRIMIDINE DERIVATIVES FOR ENHANCING ANTITUMOR ACTIVITY

This application is the 371 of PCT/US92/02434, filed Mar. 30, 1992.

BACKGROUND OF THE INVENTION

This invention relates to 2,4-diaminopyrimidines and their use as sensitizers of tumor cells to anticancer agents.

In cancer chemotherapy the effectiveness of anticancer drugs is often limited by the resistance of tumor cells. Some tumors such as of the colon, pancreas, kidney and liver are generally innately resistant, and other responding tumors often develop resistance during the course of chemotherapy. The phenomena of multidrug resistance (MDR) is characterized by the tumor cell's cross-resistance to structurally unrelated drugs. The drugs which are the target of resistance include adriamycin, daunomycin, vinblastine, vincristine, actinomycin D and etoposide. The resistance cells are often associated with over-expression of the mdr1 gene. This gene product is a family of 140–220 kd trans-membrane phosphoglycoprotein (P-glycoprotein) which functions as an ATP-dependent efflux pump. Thus, it has been postulated that this efflux mechanism keeps the intracellular level of the anticancer drug low, allowing the tumor cells to survive.

In recent years various substances such as verapamil, nifedipine and diltiazem have been used in in vitro experimental systems to reverse the MDR phenomena. More recently some of these agents have been tested clinically as MDR reversing agents. Little efficacy has been observed with verapamil or trifluoroperazine. Thus, there is a need for an effective MDR reversing agent.

Fukazawa, et al. describes a series of heterocyclic compounds (EP Application No. 89310235.0) useful as anticancer-drug reinforcing agents. This same utility is also claimed for a series of pteridine derivatives (EP Application No. 89117610.9).

Tomino, et al. (EP Application No. 89313595.4) claims a series of pyrimidines, including 2,4-diaminopyrimidines, useful in the treatment of neurological diseases.

A series of 2,4,6-triaminopyrimidine-N-oxides (U.S. Pat. No. 4,945,093) are described as being useful for promoting hair growth.

SUMMARY OF THE INVENTION

The compounds of the present invention are of the formula

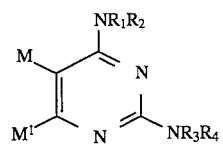

and the pharmaceutically acceptable salts thereof wherein M is hydrogen, alkoxy of one to three carbon atoms, alkyl of one to three carbon atoms or benzyl optionally substituted by one or two alkoxy substituents each having one to three carbon atoms, chloro, fluoro, amino, alkylamino of one to three carbon atoms, dialkylamino of two to six carbon atoms or trifluoromethyl; $M^1$ is hydrogen, amino, alkylamino of one to three carbon atoms, dialkylamino of two to six carbon atoms, alkyl of one to three carbon atoms, fluoro or chloro; $R_1$ is aralkyl of the formula

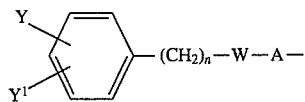

wherein n is an integer of 0 or 1, W is O, S or a chemical bond, A is alkylene of one to four carbon atoms, Y and $Y^1$ are each hydrogen, alkyl of one to three carbon atoms, alkoxy of one to three carbon atoms, fluoro, chloro, trifluoromethyl, amino, alkylamino of one to three carbon atoms or dialkylamino of two to six carbon atoms and Y and $Y^1$ when taken together are ethylenedioxy or methylenedioxy; $R_2$ is hydrogen or alkyl of one to eight carbon atoms; $R_1$ and $R_2$ when taken together with the nitrogen atom to which they are attached form a moiety of the formula

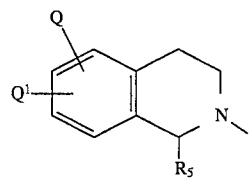

where $R_5$ is hydrogen, alkyl of one to three carbon atoms or dialkoxyphenylalkyl said alkoxy having one to three carbon atoms and said alkyl having from one to three carbon atoms, Q and $Q^1$ are each hydrogen, alkyl of one to three carbon atoms, alkoxy of one to three carbon atoms, fluoro, chloro, trifluoromethyl, amino, alkylamino of one to three carbon atoms or dialkylamino of two to six carbon atoms and Q and $Q^1$ taken together are methylenedioxy or ethylenedioxy; $R_3$ is aralkyl of the formula

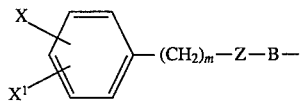

where m is an integer of 0 or 1, Z is O, S or a chemical bond, B is alkylene of one to four carbon atoms, X and $X^1$ are each hydrogen, alkyl of one to three carbon atoms, alkoxy of one to three carbon atoms, fluoro, chloro, trifluoromethyl, amino, alkylamino of one to three carbon atoms or dialkylamino of two to six carbon atoms and X and $X^1$ taken together are methylenedioxy or ethylenedioxy; $R_4$ is hydrogen or alkyl of one to four carbon atoms; and $R_3$ and $R_4$ when taken together with the nitrogen atom to which they are attached form a moiety of the formula

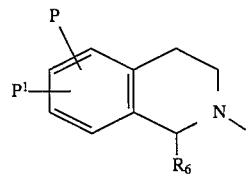

where $R_6$ is hydrogen or dialkoxybenzyl said alkoxy having one to three carbon atoms, P and $P^1$ are each hydrogen, alkyl of one to three carbon atoms, alkoxy of one to three carbon atoms, fluoro, chloro, trifluoromethyl, amino, alkylamino of one to three carbons atoms or dialkylamino of two to six carbon atoms, or P and $P^1$ when taken together are methylenedioxy or ethylenedioxy.

A preferred group of compounds are those wherein $M^1$ is hydrogen or alkyl of one to three carbon atoms, $R_1$ and $R_2$ taken together with the nitrogen to which they are attached are

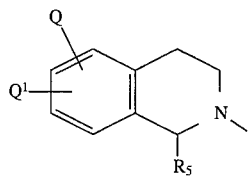

where Q is 6-methoxy, $Q^1$ is 7-methoxy and $R_3$ and $R_4$ taken together with the nitrogen to which they are attached are

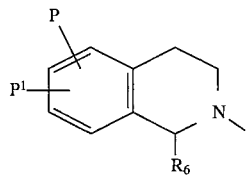

where P is 6-methoxy and $P^1$ is 7-methoxy. Especially preferred within this group are the compounds where M is hydrogen, $M^1$ is hydrogen, $R_5$ is 3,4-dimethoxybenzyl and $R_6$ is 3,4-dimethoxybenzyl and where M is hydrogen, $M^1$ is hydrogen, $R_5$ is 3,4-dimethoxybenzyl and $R_6$ is hydrogen.

A second group of preferred compounds are those where M is dialkoxybenzyl, $M^1$ is hydrogen, $R_1$ and $R_2$ taken together with the nitrogen to which they are attached are

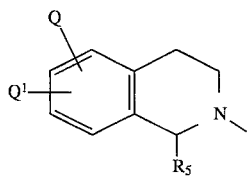

where Q is 6-methoxy and $Q^1$ is 7-methoxy, $R_3$ is aralkyl of the formula

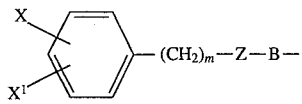

where m is 0, Z is a chemical bond and B is ethylene and $R_4$ is hydrogen. Especially preferred within this group are the compounds where M is 3,4-dimethyoxybenzyl, $R_5$ is hydrogen, X is 2-chloro and $X^1$ is hydrogen, where M is 3,4-dimethoxybenzyl, $R_5$ is 3,4-dimethoxybenzyl, X is 2-chloro and $X^1$ is hydrogen.

A third group of preferred compounds are those wherein M is hydrogen, $M^1$ is hydrogen or alkyl of one to three carbon atoms, $R_3$ is aralkyl of the formula

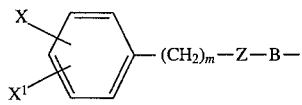

where m is 0, Z is a chemical bond and B is ethylene, $R_4$ is hydrogen and $R_1$ and $R_2$ taken together with the nitrogen to which they are attached are

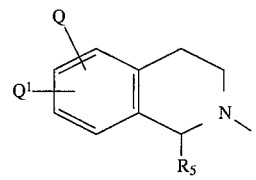

where Q is 6-methoxy and $Q^1$ is 7-methoxy. Especially preferred within this group are compounds where $M^1$ is methyl, X is 3-methoxy, $X^1$ is 4-methoxy and $R_5$ hydrogen, where $M^1$ is hydrogen, X is 2-methoxy, $X^1$ is 3-methoxy and $R_5$ is 3,4-dimethoxybenzyl, where $M^1$ is hydrogen, X is 2-chloro, $X^1$ is hydrogen and $R_5$ is 3,4-dimethoxybenzyl, where $M^1$ is hydrogen, X and $X^1$ together are 3,4-methylenedioxy and $R_5$ is 3,4-dimethoxybenzyl and where $M^1$ is methyl, X is 2-chloro, $X^1$ is hydrogen and $R_5$ is 3,4-dimethoxybenzyl.

The present invention also includes a method of inhibiting a P-glycoprotein in a mammal in need of such treatment which comprises administering to said mammal a P-glycoprotein inhibiting amount of a compound of formula I. Preferred is the method where the mammal is a human suffering from cancer and said compound is administered before, with or after the administration to said human of an anticancer effective amount of a chemotherapeutic agent.

Also included is a pharmaceutical composition for administration to a mammal which comprises a P-glycoprotein inhibiting amount of a compound of formula I, a pharmaceutically acceptable carrier and, optionally, an anticancer effective amount of a chemotherapeutic agent.

As previously indicated, the compounds of formula (I) form pharmaceutically acceptable acid addition salts. Said pharmaceutically acceptable acid addition salts include, but are not limited to, those with HCl, HBr, $HNO_3$, $H_2SO_4$; $H_3PO_4$, $CH_3SO_3H$, $p\text{-}CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt.

As one skilled in the art recognized, compounds of formula I have the potential for containing asymmetric carbon atoms. All these potential isomers are considered within the scope of the present invention.

DETAILED DESCRIPTION OF THE INVENTION

Compounds of the present invention are prepared with the reaction of a 2,4-dichloropyrimidine with an equivalent of an appropriate amine, $R_1R_2NH$, followed by the reaction of the product, a 2-chloro-4-aminopyrimidine derivative, with a second equivalent of an appropriate amine, $R_3R_4NH$.

In a more detailed description of the procedure, one molar equivalent of an optionally substituted 2,4-dichloropyrimidine and one molar equivalent of a tertiary amine-acid scavenger, such as triethylamine, N-methylmorpholine or diethylisopropylamine and one molar equivalent of an amine, $R_1R_2NH$, are combined in an anhydrous solvent such as dimethylacetamide, dioxane, methylene chloride or N-methyl-2-pyrrolidone and maintained at from 0° C. to about 25° C. for a period of 1 to 48 hours.

The reaction mixture can be filtered and the filtrate concentrated to dryness in vacuo, or the reaction mixture can be quenched in water and the intermediate product either filtered or extracted with a water immiscible solvent such as methylene chloride or ethyl acetate. Removal of the extracting solvent provides the desired product. Frequently, the residual can be induced to crystallize by trituration with an organic solvent, and further purified by recrystallization or column chromatography.

The second step of the sequence leading to the products of the present invention consists of combining one molar equivalent of the appropriate 2-chloro-4-aminopyrimidine with either two molar equivalents of an amine, $R_3R_4NH$, or one equivalent of said amine and one equivalent of a tertiary amine-acid scavenger as described above in a reaction-inert solvent such as ethoxyethoxyethanol, butanol, amyl alcohol or cyclohexanol for a period of 5 minutes to several hours at reaction temperatures of 100°–200° C.

The reaction mixture can be cooled to room temperature and treated with a 1-N solution of an appropriate acid, such as hydrochloric acid to give a precipitate of the desired product as the hydrochloride salt. Other acids would give the corresponding acid addition salt. In instances where the acid addition salt does not precipitate the free base product can be isolated by chromatographing the crude material on silica gel using an eluant such as chloroform, ethyl acetate, diethyl ether, methanol, methylene chloride, ethanol or mixtures thereof and subsequently converted to the acid addition salt product. The products are isolated by removing the eluting solvents in vacuo. Purification of the product can be done by recrystallization.

Generation of the free base from an acid addition salt can readily be carried out by treating an aqueous solution or suspension of the salt with at least one equivalent of an organic or inorganic base followed by extraction of the free base product with a water immiscible solvent such as ethyl acetate or methylene chloride. Removal of the solvent gives the desired base.

Compounds of formula I are inhibitors of the functions of P-glycoprotein, particularly human mdr 1 protein or P-glycoprotein related and membrane associate proteins which are participating in the transport of xenobiotics or proteins across membranes e.g., cell membranes of eukariotic and proeukariotic origin e.g., pmfdr, however not exclusive or restricted to these examples.

Compounds enclosed in general formula I are useful in combination chemotherapy of cancer, malaria, viral infections such as AIDS, in therapy of septic shock syndrome or inflammation and may be useful in enhancing the tissue penetration of drugs where the penetration of these xenobiotics is limited due to the presence of P-glycoprotein or P-glycoprotein related functional proteins. Compounds of formula I increase the activity/efficacy of adriamycin, daunomycin, epipodophyllotoxin congoners, actinomycin D, emetin, vincristin, vinblastin, chloroquine, anthracyclin antibiotics and of drugs which are structurally and functionally related to the above mentioned examples, in particular when the activity of these drugs has been shown to be limited due to the presence and function of P-glycoprotein, e.g. human mdr 1 protein or P-glycoprotein related proteins.

The compounds of the present invention are evaluated as potentiators of chemotherapeutic agents using a Cellular Drug Retention Assay. This assay was designed to study the effect of compounds on cellular retention of radiolabeled drug. In this case 14C-adriamycin retention by multidrug resistant human carcinoma cells, KBV1, is measured.

KBV1 cells are routinely grown in tissue culture as monolayers in DMEM high glucose medium containing 1 µg/ml vinblastine 10% heat inactivated fetal calf serum and supplemented with Glutamine, Pen-Strep and Garamycin.

The assay protocol (described below) should be applicable, with minor modifications, to a wide variety of cell lines grown in tissue culture.

Assay Protocol:

(1) Seed replicate 6-well tissue culture plates with 1.2× 10E6 cells per 2 ml per well in absence of Vinblastine;

(2) Incubate 24 hrs at 37° C. in a humidified incubator (5% $CO_2$);

(3) Aspirate off the spent media and overlay monolayers with 2 ml/well of fresh medium that is 2 µM in Adriamycin (2 µM unlabeled Adriamycin+20000 cpm of $^{14}$C-Adriamycin) and the test agent at concentrations varying from 0 to 100 µM;

(4) Following incubation for 3 hours at 37° C. in a humidified incubator, remove media and wash monolayers twice with 2 ml of ice-cold buffered saline;

(5) Detach monolayers using 0.5 ml of trypsin/EDTA, collect detached cells and transfer to scintillation vial. Rinse wells once with 0.5 ml of buffered saline and add to the same vial containing cells;

(6) Add 5 ml of Beckman Ready-Sare™ scintillation fluid to vial, vortex and determine radioactivity per sample using a scintillation counter (10 minutes per sample);

(7) For background control: pre-incubate monolayers at 4° C. for 15 minutes then remove media and add fresh ice-cold media containing Adriamycin (see step 3). Following incubation for 3 hours at 4° C. remove media and wash monolayers twice with 2 ml ice-cold buffered saline, then proceed as in step 5;

(8) Results are expressed as T/C and ED3x values as defined below:

T/C=pmoles Adr per 10E6 cells treated with test agent/ pmoles Adr per 10E6 untreated cells ED3x=concentration of test agent that produces a 3 fold increase in cellular accumulation of radiolabeled Adr, i.e. T/C=3.

Calculations

Specific cpm=[sample cpm−background cpm]

Specific activity=[cpm/total conc. of Adr]

pmoles Adr=[specific cpm/specific activity]

pmoles Adr per 10E6 cells=[(pmoles Adr per well/number of cells per well)× 10E6 cells]

As previously mentioned compounds of the present invention and salts thereof are useful in potentiating the anticancer effects of chemotherapeutic agents. Such agents can include adriamycin, daunomycin, aclacinomycin A, actinomycin C, actinomycin D, mithramycin, tomaymycin, vinblastine, maytansine, bruceantin, homoharrintonin, anguindin, neocarzinostatin, mitomycin C and anthramycin.

The compounds of the present invention can be administered with, 24 hours before or up to 72 hours after the administration of the chemotherapeutic agents. When administered with said agents, they can be taken either separately or coadministered in the same formulation.

The compounds of the present invention whether taken separately or in combination with an anticancer agent, are generally administered in the form of pharmaceutical compositions comprising at least one of the compounds of formula I and optionally a chemotherapeutic agent, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like, and, for parenteral administration, in the form of injectable solutions or suspensions, and the like.

For use in the potentiation of anticancer agents in a mammal, including man, a compound of formula I is given in an amount of about 0.5–100 mg/kg/day, in single or divided doses. A more preferred dosage range is 2–50 mg/kg/day, although in particular cases, at the discretion of the attending physician, doses outside the broader range may be required. The preferred route of administration is generally oral, but parenteral administration (e.g. intramuscular, intravenous, intradermal) will be preferred in special cases, e.g., where oral absorption is impaired as by disease, or where the patient is unable to swallow.

The present invention is illustrated by the following examples, but is not limited to the details or scope thereof.

EXAMPLE 1

2-(2-Chlorophenethylamino)-4-(1,2,3,4-tetrahydro-6,7-dimethoxyisoquinol-2-yl)-5- (3,4-dimethoxybenzyl)-pyrimidine (M=3,4-$(CH_3O)_2C_6H_3CH_2$—; $M^1$=H; $R_1R_2N$=1,2,3,4-tetrahydro-6,7-$(CH_3O)_2$-isoquinol-2-yl; $R_3$=2-$ClC_6H_4(CH_2)_2$—; and $R_4$=H)

A. 5-(3,4-Dimethoxybenzyl)uracil

A solution of 5.0 g of 5-hydroxymethyluracil, 150 ml of veratrole and 0.5 ml of concentrated hydrochloric acid was heated at 140° C. for one hour. The precipitate was filtered, washed with ether and recrystallized from hot methanol, 6.85 g, $M^+$ 263.20.

B. 2,4-Dichloro-5-(3,4-dimethoxybenzyl)pyrimidine

A mixture of 4.7 g of the product of Example 1A and 125 ml of phosphorus oxychloride was heated to reflux overnight. The excess phosphorus oxychloride was removed in vacuo and the residue poured into ice water. The aqueous was extracted with methylene chloride and the extracts combined and dried over sodium sulfate. The residue, after removal of the methylene chloride, was chromatographed on silica gel (methylene chloride) to give 4.92 g of the desired intermediate, $M^+$ 299.0.

C. 2-Chloro-4-(6,7-dimethoxy-1,2,3,4-tetrahydroisoquinol-2-yl)-5-(3,4-dimethoxybenzyl)pyrimidine A solution of 2.0 g of the compound of Example 1B, 1.54 g of 6,7-dimethoxy-1,2,3,4-tetrahydroisoquinoline hydrochloride and 1.73 g of diisopropylethylamine in 125 ml of dioxane was heated to reflux overnight. The solvent was removed in vacuo and the residue chromatographed on silica gel (4% ethyl acetate-methylene chloride) to give 2.27 g of product, $M^+$ 456.10.

D. 2-(2-Chlorophenethylamino)-4-(1,2,3,4-tetrahydro-6,7-dimethoxyisoquinol-2-yl)-5-(3,4-dimethoxybenzyl)pyrimidine A mixture of 300 mg of the product of Example 1C, 102 mg of 2-chlorophenethylamine and 85 mg of diisopropylethylamine in 1 ml of 2-(2-ethoxyethoxy)ethanol was heated to 160° C. for two hours. The solvent was removed in vacuo and the residue chromatographed on silica gel (2% methanol-methylene chloride) to give 230 mg of product, m.p. 140°–141° C., $M^+$ 575.30.

EXAMPLES 2–16

Starting with the appropriate reagents and employing the procedures of Example 1, the following compounds were prepared:

Example 2: M=H; $M^1$=6-$CH_3$; $R_5$=H; $Q^1$=6-$CH_3O$; $Q^2$=7-$CH_3O$; $R_3$=2,3-$(CH_3O)_2C_6H_3(CH_2)$—; and $R_4$=H; m.p. 224°–226.5° C., $M^+$ 465.00.

Example 3: M, $M^1$=H; $R_5$=H; $Q^1$=6-$CH_3O$; $Q^2$=7-$CH_3O$; $R_3NR_4$= m.p. 151°–153° C., $M^+$ 613.20.

Example 4: M, $M^1$=H; $R_5$=3,4-$(CH_3O)_2C_6H_3CH_2$—; $Q^1$=6-$CH_3O$; $Q^2$=7-$CH_3O$; $R_3NR_4$= m.p. 138°–142° C., $M^+$ 763.40.

Example 5: M, $M^1$=H; $R_5$=3,4-$(CH_3O)_2C_6H_3CH_2$—; $Q^1$=6-$CH_3O$; $Q^2$=7-$CH_3O$; $R_3$=3,4-$(CH_3O)_2C_6H_3(CH_2)_2$—; and $R_4$=H; m.p. 174°–175° C., $M^+$ 601.50.

Example 6: M=H; $M^1$=6-$CH_3$; $R_5$=H; $Q^1$=6-$CH_3O$; $Q^2$=7-$CH_3O$; $R_3$=3,4-$(CH_3O)_2C_6H_3(CH_2)_2$—; and $R_4$=H; m.p. 72°–76° C., $M^+$ 465.0.

Example 7: M, $M^1$=H; $R_5$=3,4-$(CH_3O)_2C_6H_3CH_2$—; $Q^1$=6-$CH_3O$; $Q^2$=7-$CH_3O$; $R_3$=2,3-$(CH_3O)_2C_6H_3(CH_2)_2$—; and $R_4$=H; m.p. 69°–72° C., $M^+$ 601.40.

Example 8: M, $M^1$=H; $R_5$=3,4-$(CH_3O)_2C_6H_3CH_2$—; $Q^1$=6-$CH_3O$; $Q^2$=7-$CH_3O$; $R_3$=2-$ClC_6H_4(CH_2)_2$—; and $R_4$=H; m.p. 73°–75° C., $M^+$ 575.30.

Example 9: M, $M^1$=H; $R_5$=3,4-$(CH_3O)_2C_6H_3CH_2$—; $Q^1$=6-$CH_3O$; $Q^2$=7-$CH_3O$; $R_3$=3,4-$(CH_2O_2)C_6H_3(CH_2)_2$—; and $R_4$=H; m.p. 118°–122° C., $M^+$ 585.3.

Example 10: M, M$^1$=H; R$_5$=3,4-(CH$_3$O)$_2$C$_6$H$_3$CH$_2$—; Q$^1$=6-CH$_3$O; Q$^2$=7-CH$_3$O; R$_3$=4-CH$_3$OC$_6$H$_4$O(CH$_2$)$_2$—; and R$_4$=H; m.p. 160°–162° C., M$^+$ 587.3.

Example 11: M=H; M$^1$=6-CH$_3$; R$_5$=3,4-(CH$_3$O)$_2$C$_6$H$_3$CH$_2$—; Q$^1$=6-CH$_3$O; Q$^2$=7-CH$_3$O; and R$_3$NR$_4$=

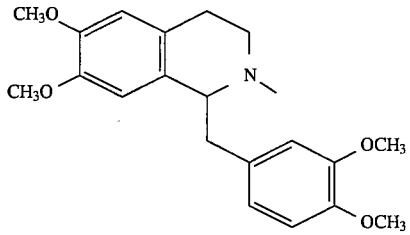

m.p. 190°–192° C., M$^+$ 777.3.

Example 12: M=H; M$^1$=6-CH$_3$; R$_5$=H; Q$^1$=6-CH$_3$O; Q$^2$=7-CH$_3$O; R$_3$=2-ClC$_6$H$_4$(CH$_2$)$_2$—; and R$_4$=H; m.p. 174°–177° C., M$^+$ 439.0.

Example 13: M=H; M$^1$=6-CH$_3$; R$_5$=H; Q$^1$=6-CH$_3$O; Q$^2$=7-CH$_3$O; R$_3$=3,4-(CH$_3$O)$_2$C$_6$H$_3$(CH$_2$)$_2$—; and R$_4$=H; m.p. 170°–171° C., M$^+$ 615.3.

Example 14: M=H; M$^1$=6-CH$_3$; R$_5$=3,4-(CH$_3$O)$_2$C$_6$H$_3$CH$_2$; Q$^1$=6-CH$_3$O; Q$^2$=7-CH$_3$O; R$_3$=2,3-(CH$_3$O)$_2$C$_6$H$_3$(CH$_2$)$_2$—; and R$_4$=H; m.p. 110°–112° C., M$^+$ 615.3.

Example 15: M=H; M$^1$=6-CH$_3$; R$_5$=3,4-(CH$_3$O)$_2$C$_6$H$_3$CH$_2$; Q$^1$=6-CH$_3$O; Q$^2$=7-CH$_3$O; R$_3$=2-ClC$_6$H$_4$(CH$_2$)$_2$—; and R$_4$=H; m.p. 100°–102° C., M$^+$ 589.3.

Example 16: M=5-CH$_3$; M$^1$=6-CH$_3$; R$_5$=H; Q=6-CH$_3$O; Q$^2$=7-CH$_3$O; R$_3$=3,4-(CH$_3$O)$_2$C$_6$H$_3$(CH$_2$)$_2$—; and R$_4$=H; m.p. 117°–118° C., M$^+$ 478.3.

EXAMPLES 17–20

Employing the procedure of Example 1 and starting with required reagents, the following compounds were prepared:

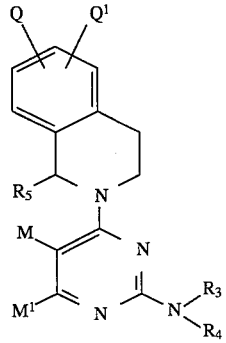

Example 17: M=3,4-(CH$_3$O)$_2$C$_6$H$_3$CH$_2$—; M$^1$=H; R$_5$=H; Q$^1$=6-CH$_3$O; Q$^2$=7-CH$_3$O; R$_3$=3,4-(CH$_3$O)$_2$C$_6$H$_3$(CH$_2$)$_2$—; and R$_4$=H; m.p. 89°–91° C., M$^+$ 601.40.

Example 18: M=3,4-(CH$_3$O)$_2$C$_6$H$_3$CH$_2$—; M$^1$=H; R$_5$=H; Q$^1$=6-CH$_3$O; Q$^2$=7-CH$_3$O; R$_3$=2,3-(CH$_3$O)$_2$C$_6$H$_3$(CH$_2$)$_2$—; and R$_4$=H; m.p. 89°–91° C., M$^+$ 601.4.

Example 19: M=3,4-(CH$_3$O)$_2$C$_6$H$_3$CH$_2$—; M$^1$=H; R$_5$=3,4-(CH$_3$O)$_2$C$_6$H$_3$CH$_2$—; Q$^1$=6-CH$_3$O; Q$^2$=7-CH$_3$O; R$_3$=2-ClC$_6$H$_4$(CH$_2$)$_2$—; and R$_4$=H; m.p. 90°–95° C., (free base) M$^+$ 725.50.

Example 20: M=H; M$^1$=6-Cl; R$_5$=H; Q$^1$=6-CH$_3$O; Q$^2$=7-CH$_3$O; R$_3$=2-ClC$_6$H$_4$(CH$_2$)$_2$—; and R$_4$=H; m.p. (HCl salt) 129°–131° C., M$^+$ 459.10.

EXAMPLE 21

2-(1-[3,4-Dimethoxybenzyl]-6,7-dimethoxy-1,2,3,4-tetrahydroisoquinol-2-yl)-4- (3,4-dimethoxyphenethylamino)pyrimidine hydrochloride (M and M$^1$=H; R$_1$R$_2$N=3,4-(CH$_3$O)$_2$C$_6$H$_3$(CH$_2$)$_2$NH; and R$_3$R$_4$N=1,2,3,4-tetrahydro-1-(3,4-dimethoxybenzyl)-6,7-dimethoxyisoquinol-2-yl)

A mixture of 149 mg of 2,4-dichloropyrimidine, 181 mg 2-(3,4-dimethoxyphenyl)ethylamine and triethylamine (111 mg) in 2 mL of 2-(2-ethoxyethoxy)ethanol was stirred at room temperature for 4 hours. After this period, tetrahydropapaverine hydrochloride (300 mg) and triethylamine (222 mg) were added and the mixture was heated at 170° C. under nitrogen for 1.5 hours. The precipitate was filtered off and the solvent was removed under reduced pressure. The residue was chromatographed on silica gel using 2.5% methanol in methylene chloride (V:V) to give 45 mg (7.5%) of solid. This solid was treated with 1N methanolic hydrogen chloride to give the title compound as an amorphous solid: m.p. 48°–51° C., M$^+$ 601.

EXAMPLES 22–24

Starting with the appropriate reagents and employing the procedure of Example 1, the following products were prepared:

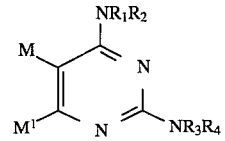

Example 22: M and M$^1$=H; R$_1$=C$_6$H$_5$CH$_2$; R$_2$=CH$_3$; R$_3$=3,4-(CH$_3$O)$_2$C$_6$H$_3$(CH$_2$)$_2$—; and R$_4$=H; m.p. 109°–111° C., M$^+$ 379.

Example 23: M and M$^1$=H; R$_1$=C$_6$H$_5$CH$_2$; R$_2$=CH$_3$; R$_3$=2,3-(CH$_3$O)$_2$C$_6$H$_3$(CH$_2$)$_2$—; and R$_4$=H; m.p. 128°–129° C., M$^+$ 379.

Example 24: M and M$^1$=H; R$_1$=3,4-(CH$_3$O)$_2$C$_6$H$_3$(CH$_2$)$_2$—; R$_2$=H; R$_3$=3,4-(CH$_3$O)$_2$C$_6$H$_3$(CH$_2$)$_2$; and R$_4$=H; m.p. 100°–102° C., M$^+$ 439.2.

PREPARATION A

Starting with the appropriate reagents and following the procedure of Example 1C, the following intermediates were prepared:

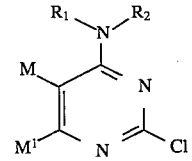

| M | M¹ | R₁R₂N | m.p., °C. |
|---|---|---|---|
| H | CH₃ | 3,4-dimethoxyphenethyl-N-methyl | 138–141 |
| H | H | 3,4-dimethoxyphenethyl-N-methyl | 149–151 |
| H | H | 6,7-dimethoxy-1-(3,4-dimethoxybenzyl)-tetrahydroisoquinolin-2-yl-methyl | 146–148 |
| H | CH₃ | 6,7-dimethoxy-1-(3,4-dimethoxybenzyl)-tetrahydroisoquinolin-2-yl-methyl | 125–126 |
| 3,4-dimethoxybenzyl | H | 6,7-dimethoxy-1-(3,4-dimethoxybenzyl)-tetrahydroisoquinolin-2-yl-methyl | 125–127 |
| H | Cl | 6,7-dimethoxy-tetrahydroisoquinolin-2-yl-methyl | 129–131 |
| CH₃ | CH₃ | 6,7-dimethoxy-tetrahydroisoquinolin-2-yl-methyl | 134–136 |
| 3,4-dimethoxybenzyl | H | 6,7-dimethoxy-tetrahydroisoquinolin-2-yl-methyl | 145–147 |
| H | H | C₆H₅CH₂—N(CH₃)— | oil |

We claim:

1. A compound of the formula

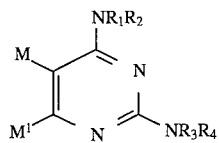

I or the pharmaceutically acceptable acid addition salt thereof wherein M is hydrogen, alkoxy having one to three carbon atoms, alkyl having one to three carbon atoms or benzyl optionally substituted by one or two alkoxy substituents each having one to three carbon atoms, amino, alkylamino having one to three carbon atoms, dialkylamino having two to six carbon atoms, fluoro, chloro or trifluoromethyl; M¹ is hydrogen, amino, alkylamino having one to three carbon atoms, dialkylamino having two to six carbon atoms, alkyl having one to three carbon atoms, fluoro or chloro; $R_1$ is aralkyl of the formula

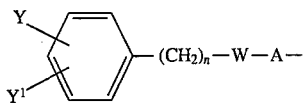

wherein n is an integer of 0 or 1, W is O, S or a chemical bond, A is alkylene having one to four carbon atoms, Y and $Y^1$ are each hydrogen, alkyl having one to three carbon atoms, alkoxy having one to three carbon atoms, fluoro, chloro, trifluoromethyl, amino, alkylamino having one to three carbon atoms or dialkylamino having two to six carbon atoms and Y and $Y^1$ when taken together are ethylenedioxy or methylenedioxy; $R_2$ is hydrogen or alkyl having one to eight carbon atoms; $R_1$ and $R_2$ when taken together with the nitrogen atom to which they are attached form a moiety of the formula

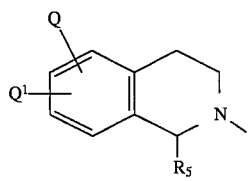

wherein $R_5$ is hydrogen, alkyl having one to three carbon atoms or dialkoxyphenylalkyl said alkoxy having one to three carbon atoms and said alkyl having from one to three carbon atoms, Q and $Q^1$ are each hydrogen, alkyl having one to three carbon atoms, alkoxy having one to three carbon atoms, fluoro, chloro, amino, alkylamino having one to three carbon atoms, trifluoromethyl or dialkylamino having two to six carbon atoms and Q and $Q^1$ taken together are methylenedioxy or ethylenedioxy; $R_3$ is aralkyl of the formula

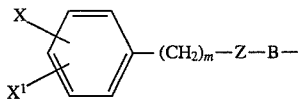

wherein m is an integer of 0 or 1, Z is O, S or a chemical bond, B is alkylene of one to four carbon atoms, X and $X^1$ are each hydrogen, alkyl having one to three carbon atoms, alkoxy having one to three carbon atoms, fluoro, chloro, trifluoromethyl, amino, alkylamino having one to three carbon atoms or dialkylamino having two to six carbon atoms and X and $X^1$ taken together are methylenedioxy or ethylenedioxy; $R_4$ is hydrogen or alkyl having one to four carbon atoms; and $R_3$ and $R_4$ when taken together with the nitrogen atom to which they are attached form a moiety of the formula

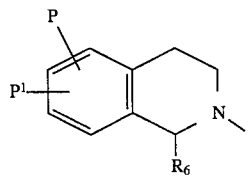

wherein P and $P^1$ are each hydrogen, alkyl having one to three carbon atoms, alkoxy having one to three carbon atoms, fluoro, chloro, trifluoromethyl, amino, alkylamino having one to three carbon atoms or dialkylamino having two to six carbon atoms, P and $P^1$ when taken together are methylenedioxy or ethylenedioxy and $R_6$ is hydrogen or dialkoxybenzyl said alkoxy having one to three carbon atoms.

2. A compound of claim 1, wherein $M^1$ is hydrogen or alkyl having one to three carbon atoms, $R_1$ and $R_2$ taken together with the nitrogen atom to which they are attached form a moiety of the formula

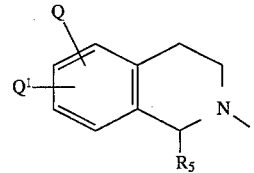

wherein Q is 6-methoxy, $Q^1$ is 7-methoxy and $R_3$ and $R_4$ when taken together with the nitrogen to which they are attached form a moiety of the formula

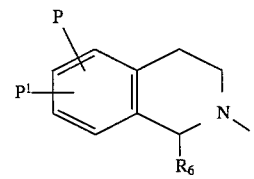

wherein P is 6-methoxy and $P^1$ is 7-methoxy.

3. The compound of claim 2, wherein M is hydrogen, $M^1$ is hydrogen, $R_5$ is 3,4-dimethoxybenzyl and $R_6$ is 3,4-dimethoxybenzyl.

4. The compound of claim 2, wherein M is hydrogen, $M^1$ is hydrogen, $R_5$ is 3,4-dimethoxybenzyl and $R_6$ is hydrogen.

5. A compound of claim 1, wherein M is dialkoxybenzyl, $M^1$ is hydrogen, $R_1$ and $R_2$ when taken together with the nitrogen atom to which they are attached form a moiety of the formula

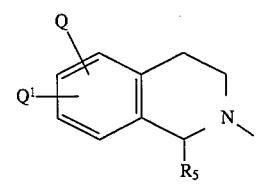

wherein Q is 6-methoxy and $Q^1$ is 7-methoxy, $R_3$ is aralkyl of the formula

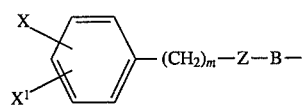

wherein m is 0, Z is a chemical bond and B is ethylene and $R_4$ is hydrogen.

6. The compound of claim 5, wherein M is 3,4-dimethoxy benzyl, $R_5$ is hydrogen, X is 2-chloro and $X^1$ is hydrogen.

7. The compound of claim 5, wherein M is 3,4-dimethoxybenzyl, $R_5$ is hydrogen, X is 3-methoxy and $X^1$ is 4-methoxy.

8. The compound of claim 5, wherein M is 3,4-dimethoxybenzyl, $R_5$ is 3,4-dimethoxybenzyl, X is 2-chloro and $X^1$ is hydrogen.

9. A compound of claim 1, wherein M is hydrogen, $M^1$ is hydrogen or alkyl having one to three carbon atoms, $R_3$ is aralkyl of the formula

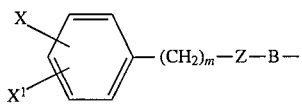

wherein m is 0, Z is a chemical bond, B is ethylene, $R_4$ is hydrogen and $R_1$ and $R_2$ taken together with the nitrogen to which they are attached from a moiety of the formula

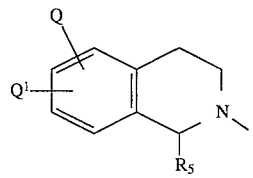

where Q is 6-methoxy and $Q_1$ is 7-methoxy.

10. The compound of claim 9, wherein $M^1$ is methyl, X is 3-methoxy, $X^1$ is 4-methoxy and $R_5$ is hydrogen.

11. The compound of claim 9, wherein $M^1$ is hydrogen, X is 2-methoxy, $X^1$ is 3-methoxy and $R_5$ is 3,4-dimethoxybenzyl.

12. The compound of claim 9, wherein $M^1$ is hydrogen, X is 2-chloro, $X^1$ is hydrogen and $R_5$ is 3,4-dimethoxybenzyl.

13. The compound of claim 9, wherein $M^1$ is hydrogen, X and $X^1$ together are 3,4-methylenedioxy and $R_5$ is 3,4-dimethoxybenzyl.

14. The compound of claim 9, wherein $M^1$ is methyl, X is 2-chloro, $X^1$ is hydrogen and $R_5$ is 3,4-dimethoxybenzyl.

* * * * *